United States Patent [19]

Larock

[11] 4,026,957

[45] May 31, 1977

[54] SYMMETRICAL CONJUGATED DIENE AND POLYENE SYNTHESIS VIA VINYLMERCURIC SALTS

[75] Inventor: Richard Craig Larock, Ames, Iowa

[73] Assignee: Iowa State University Research Foundation, Inc., Ames, Iowa

[22] Filed: Apr. 30, 1976

[21] Appl. No.: 681,783

[52] U.S. Cl. .................. 260/666 A; 260/453 R; 260/563 R; 260/586 R; 260/617 R; 260/666 PY; 260/668 R; 260/680 B
[51] Int. Cl.$^2$ .......................................... C07C 1/00
[58] Field of Search ..... 260/680 B, 666 PY, 668 R, 260/666 A, 677 A, 678

[56] References Cited

UNITED STATES PATENTS 3,361,840   1/1968   Kohll et al. .................. 260/680 B

*Primary Examiner*—Delbert E. Gantz
*Assistant Examiner*—Joseph A. Boska
*Attorney, Agent, or Firm*—Zarley, McKee, Thomte, Voorhees & Sease

[57] ABSTRACT

Vinylmercuric halide salts undergo reaction with palladium (II) dimerization promoting agents, preferably in a highly polar organic solvent at low temperatures to provide essentially quantative yields of conjugated dienes. Importantly, the reaction is stereospecific and is especially valuable for synthesis of functionally substituted dienes and symmetrical polyenes.

14 Claims, No Drawings

SYMMETRICAL CONJUGATED DIENE AND POLYENE SYNTHESIS VIA VINYLMERCURIC SALTS

BACKGROUND OF THE INVENTION

Conjugated dienes are of considerable importance in organic chemistry in and of themselves. In addition, they are extremely important for use in the well-known Diels-Alder reaction. Many conjugated dienes are used as intermediates for synthesis reactions and as monomers for the formation of polymeric reaction products. For example, the preparation of polybutadiene rubber.

One problem often encountered with prior art processes for the formation of conjugated dienes is that the reaction procedures often are unsuitable for the preparation of functionally substituted dienes. Thus, if the diene being prepared is functionally substituted with, for example, a carboxyl group, a carbonyl group, an amino group, an ester group, or the like, often the reactive site in any synthesis reaction will be at the functional group rather than the formation of the desired conjugated diene. As a result, very few functional groups have been incorporated into these reactions.

In addition, the preparation of conjugated dienes often encounters the difficulty that the stereospecificity of the reaction starting material is lost in the coupling procedure to prepare the conjugated diene. This is important in many syntheses since the stereochemistry can and indeed often does affect the ultimate reaction properties of any polymers which are formed.

Accordingly, there is a real need in the art for the development of a new process for the preparation of symmetrical conjugated dienes and polyenes which both tolerates functionality and which produces symmetrical dienes, stereospecifically in high yields. This invention has as its primary objective the satisfaction of the above described needs.

SUMMARY OF THE INVENTION

This invention relates to a method of preparing stereospecific, symmetrical, conjugated dienes which comprises reacting a vinylmercuric halide salt with a palladium (II) halide salt, preferably in a polar organic solvent, in the presence of a lithium halide salt to produce a diene which predominantly retains the stereochemistry of the vinylmercuric halide salt. The reaction produces the desired diene in nearly quantitative yield, maintains the stereochemistry of the vinylmercuric halide salt, and tolerates functional substitution on the vinylmercuric salt with the reaction occurring without any adverse effect upon the functionally substituted groups.

DETAILED DESCRIPTION OF THE INVENTION

In accordance with the process of this invention, a vinylmercuric halide of the general formula

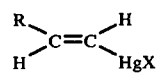

is reacted with a palladium (II) salt. In the formula for the vinylmercuric halide, X represents the anion of that compound and may be any of the common inorganic anions such as nitrate, acetate, phosphate, sulfate, chloride, bromide, iodide or the like. However, it is most preferable that X represents a monovalent inorganic anion which is a halide and more particularly is either chloride, bromide or iodide.

The value of R is not critical and depends upon the precise conjugated diene which one desires to prepare. Generally R may be hydrogen or an organic monovalent hydrocarbon radical which is either saturated or unsaturated. The radical may be functionally substituted to provide, for example, keto groups, carboxylic acid groups, hydroxy groups, ester groups, amino groups, or other functional substituents. It may be an alkyl, acyl, aryl, aralkyl, alkenyl, alkynyl, straight or branched chain, or cyclic derivatives of the above, including heterocyclics.

Preferably R is a lower, $C_{12}$ and below, straight or branched chain, saturated or unsaturated, substituted or unsubstituted, straight or branched chain, alkyl, alkenyl, phenyl, or aralkyl group.

As depicted in the general formula for the vinylmercuric halide salt, two hydrogen moieties are shown. However, it is to be understood, that, if desired, the hydrogen moieties may be replaced with organic radicals such as those previously described to represent R.

The starting material for the reaction of this invention, namely, vinylmercuric halides, are readily available through acetylene addition reactions, see for example, R. C. Larock and H. C. Brown. *J. Organometal Chem.*, 36, 1 (1972).

R. C. Larock, S. K. Gupta, and H. C. Brown, *J. Amer. Chem. Soc.*, 94, 4371 (1972).

H. Staub, K. P. Zeller and H. Leditschke, In Houben-Weyl's "Methoden der Organischen Chemie," Fourth ed., Vol. 13, G. Thieme Verlag, Stuttgart, 1974, Pt. 2b, pp 192–199.

which are incorporated herein by reference.

The previously discussed vinylmercuric compound, which is a starting material for the reaction of this invention, is reacted with a palladium (II) salt. The palladium (II) salt may be a palladium salt of any of the common inorganic anions, such as nitrate, phosphate, acetate, sulfate, chloride, bromide, iodide, or the like. Preferably, the palladium salt is a halide salt and most preferably is palladium chloride.

While the palladium (II) dimerization promoting reagent is continually referred to herein as a palladium salt, and most preferably a palladium halide salt, it should be understood that salts of other noble metals may be able to be employed in the reaction of this invention, such as platinum, iridium, rhodium, ruthenium and osmium.

Where the reaction of the vinylmercuric salt is promoted with a palladium (II) dimerization promoting agent, such as for example, palladium halide salts, it is essential that the reaction is conducted in the presence of a polar organic solvent and further, in the presence of additional amounts of the halide ions. These two conditions are essential in order to assure that the reaction is in fact stereospecific. In the absence of polar organic solvents or additional amounts of halide anions, the reaction product will be a mixture of regio and stereoisomers and in addition, the reaction yields are considerably reduced.

Any highly polar organic solvents capable of dissolving the palladium (II) salt and the vinylmercuric salt may be employed but it has been found that the yield of the diene increases steadily with the polarity of the solvent and in particular, seems to be best when the solvent is an organic phosphorus containing solvent.

Typical solvents which may be employed to produce the conjugated diene products of this invention include tetrahydrofuran, methyl cyanide, pyridine, acetone, methyl alcohol, dimethyl sulfoxide, N, N-dimethyl formamide, and organic phosphorous containing polar solvents such as hexamethylphosphoramide. The most highly preferred solvent is hexamethylphosphoramide since the highest yields of product, consistent with maintaining stereospecificity, are achieved.

As previously mentioned, in order to achieve high yields of the symmetrical conjugated dienes in accord with the synthesis reaction which employs palladium (II) chloride salts as a dimerization promoting agent, it is essential that reaction be conducted in the presence of added amounts of halide ions. By the term added amounts of halide ions is meant amounts of halide ions in excess of the amount which may otherwise be provided by the vinylmercuric salt, if that salt is a halide salt, and the palladium (II) salt if that salt is also a halide salt.

It is preferred that additional amounts of halide ions be added because such as has been found essential to providing high yields of symmetrical conjugated dienes which maintain the stereochemistry of the vinylmercuric salt. The source of the additional halide ions may be any metal salt which is soluble in the reaction solvent. Preferably the metal salt is an alkali metal halide salt with the alkali metal being sodium, potassium or lithium. Most preferably the alkali metal is lithium and the salt is lithium chloride.

Better yields of product and higher stereospecificity are also observed at lower reaction temperatures. Thus, it is preferred that the reaction be conducted at room temperature or lower temperatures. Generally satisfactory results are obtained at temperatures within the range of from about 0° C. to about 25° C. with most preferred results being obtained at temperatures of about 0° C.

To summarize for a moment, the synthesis route for the preparation of the symmetrical, stereospecific, conjugaged dienes in accord with the process of this invention may be represented by the following equation, which assumes that the vinylmercury compound is vinylmercuric chloride and which assumes that the palladium (II) salt is palladium chloride and that the added source of halide ions is lithium chloride.

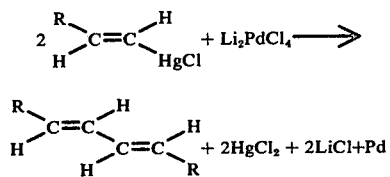

In the reaction formula, the palladium chloride is shown as a complex formed between the palladium (II) chloride salt and the lithium chloride often referred to as a coordination complex of lithium palladium chloride. The reaction is advantageous over prior art processes of preparing conjugated dienes in that it obtains the desired product in high yield, often in excess 90%.

In addition, the reaction is stereospecific and maintains the stereospecific relationship of the vinylmercuric halide so that one can predictably prepare cis or trans isomers. In addition, the reaction is highly tolerant of the presence of functional groups substituted on the R moiety or in place of the hydrogen moieties of the vinylmercuric salt. It is the entire combination of reaction conditions which produces high yields, the tolerance to functional groups, and the stereospecificity. The tolerance to functional group substitution is a characteristic of the vinylmercuric halide starting material and the vinylpalladium intermediate. The obtaining of high yields and control of the stereochemistry of the isomer produced appears to be a function of employment of the vinyl mercuric halide starting material in combination with suitable solvents and an excess of halide ions in the reaction. As can be seen, substantially different results are obtained when different solvents are employed or when reaction conditions not within those limits specified herein are employed. It is preferred that the reaction temperature be room temperature or lower since better yeilds and higher stereospecificity are observed at lower temperatures.

The following examples are offered to further illustrate but not limit the process of this invention.

EXAMPLE I (Synthesis of trans, trans-2,2,7,7-tetramethyl-3, 5-octadiene)

100 ml of hexamethylphosphoramide was added to well dried nitrogen filled 250 ml rounded bottom flask with a septum inlet. In accordance with the reaction disclosed herein, the hexamethylphosphoramide functions as a solvent for the reaction 40 mmol of anhydrous lithium chloride and 10 mmol of palladium chloride were also added to the round bottom flask. The flask was thoroughly cooled in an ice bath to a temperature of about 0° and 20 mmol of trans-3,3-dimethyl-1-butenylmercuric chloride was added rapidly while backflushing with nitrogen. The reaction mixture immediately turned black and was allowed to slowly warm to room temperature on its own and thereafter stirred overnight. In the morning activated carbon, water and pentane were added. The reaction mixture was filtered and the organic layer was separated from the aqueous layer. The aqueous layer was repeatedly extracted with pentane. The combined extracts were washed with water, dried over anhydrous sodium sulfate and evaporated, leaving 1.6 g (96%) of a very pale yellow solid which was analytically pure by GLPC and nmr analysis: mp 78°–79° (EtOH), pmr peaks (CCl$_4$) at $\delta$ 1.02 (s, 18H, CH$_3$) and 5.3–6.0 (m, 4H, vinyl). This compound was identical with an authentic sample of trans, trans-2,2,7,7 tetramethyl-3, 5-octadiene. This reaction synthesis is reported in the following table, Table I, as preparation 1.

In Table I, presented on the following page, the reaction was run under identical conditions as specified herein with the only change being the vinyl mercuric halide starting material. The starting material, the resulting dimer, and the yields are presented in Table I.

TABLE I

Synthesis of Dienes and Polyenes (Examples 2-10)

| Example | Organomercurial | Dimer | Yield, % |
|---|---|---|---|
| 1 | (CH₃)₃C-CH=CH-HgCl | (CH₃)₃C-CH=CH-CH=CH-C(CH₃)₃ | 96 |
| 2 | CH₃(CH₂)₂-CH=CH-HgCl | CH₃(CH₂)₂-CH=CH-CH=CH-(CH₂)₂CH₃ | 98 |
| 3 | CH₃(CH₂)₃-CH=CH-HgCl | CH₃(CH₂)₃-CH=CH-CH=CH-(CH₂)₃CH₃ | 100 |
| 4 | CH₃O₂C(CH₂)₈-CH=CH-HgCl | CH₃O₂C(CH₂)₈-CH=CH-CH=CH-(CH₂)₈CO₂CH₃ | 94 |
| 5 | Ph-CH=CH-HgCl | Ph-CH=CH-CH=CH-Ph | 100 |
| 6 | CH₃CH₂-C(=CH-HgCl)-CH₂CH₃ (tetrasubstituted vinylmercurial with two ethyl groups) | corresponding diene | 75 |
| 7 | Ph₂C=CH-HgCl | Ph₂C=CH-CH=CPh₂ | 100 |
| 8 | CH₃C(O)O-C(CH₃)=C(CH₃)-HgCl | CH₃C(O)O-C(CH₃)=C(CH₃)-C(CH₃)=C(CH₃)-OC(O)CH₃ | 82 |
| 9 | CH₂=C(CH₃)-CH=CH-HgCl | CH₂=C(CH₃)-CH=CH-CH=CH-C(CH₃)=CH₂ | 95 |
| 10 | CH₃-C≡C-C(CH₃)=CH-HgCl (enyne) | corresponding dimer with two enyne units | 92 |

EXAMPLES 11-28

In order to study the effect of solvent, stoichoimetry of the reaction, and the reaction temperature upon the percentage yield of desired product, and the stereospecificity of the reaction, the reaction synthesis was conducted under a variety of conditions as specified in Examples 11 through 28. Again, the basic procedure was exactly as presented in Example I herein with the exception of variations in details shown in Table II.

Table II

| Ex-ample | Vinylmercuric Chloride[a] | PdCl₂ (mmol) | LiCl (mmol) | Solvent[b] | Temp, °C | Diene Yield (%) trans, trans | cis, trans | cis, cis |
|---|---|---|---|---|---|---|---|---|
| 11 | Ph-CH=CH-HgCl | 1 | — | HMPA | 25 | <5 | — | — |
| 12 | | | 2 | | | 99 | — | — |
| 13 | | | 4 | | | 100 | — | — |
| 14 | | 2 | | | | 94 | 6 | — |
| 15 | | 1 | | C₆H₆ | | 3 | — | — |
| 16 | | | | Et₂O | | 4 | — | — |
| 17 | | | | THF | | 29 | — | — |
| 18 | | | | CH₃CN | | 50 | — | — |

Table II-continued

| Example | Vinylmercuric Chloride[a] | PdCl₂ (mmol) | LiCl (mmol) | Solvent[b] | Temp, °C | Diene Yield (%) trans, trans | cis, trans | cis, cis |
|---|---|---|---|---|---|---|---|---|
| 19 | | | | Pyridine | | 54 | — | — |
| 20 | | | | Acetone | | 57 | — | — |
| 21 | | | | CH₃OH | | 64 | — | — |
| 22 | | | | DMF | | 82 | — | — |
| 23 | | | | DMSO | | 82 | — | — |
| 24 | | | | HMPA | | 68 | 15 | — |
| 25 | n-C₄H₉\C=C/H, H/C=C\HgCl | | | | 0 | 100 | — | — |
| 26 | C₂H₅\C=C/C₂H₅, H/C=C\HgCl | | | | 25 | — | 5 | 75 |
| 27 | | | | | 0 | — | — | 75 |
| 28 | | 2 | | | | — | 7 | 33 |

[a]Two mmol.
[b]Ten ml.

As can be seen from Examples 11–28, the importance of solvent, temperature and additional halides is demonstrated. For example, styrylmercuric chloride reacts rapidly with palladium chloride with or without added lithium chloride, but only in the presence of added lithium chloride is the diene obtained in good yield. Excess lithium chloride seems to have no effect. On the other hand, excess amounts of the palladium (II) salt dimerization promoting agent decreases the stereospecificity of the reaction as well as the yield of diene, see for example, Examples 14 and 28. The precise choice of solvent also plays a critical role in the reactions. The yield of diene increases steadily with the polarity of the solvent, with hexamethylphosphoramide being the preferred solvent. Better yields and higher stereospecificity are also observed at lower temperatures.

For the sake of clarity, THF in Table II refers to tetrahydrofuran, DMF refers to N,N-dimethylformamide, DMSO refers to dimethyl sulfoxide, and HMPA refers to hexamethylphosphoramide.

As can be seem from the examples presented herein, a convenient, simple, synthesis route for stereospecific conjugated dienes and polyenes via the use of vinylmercuric compounds as starting materials, has been provided.

What is claimed is:

1. A method of preparing symmetrical conjugated hydrocarbyl dienes, said method comprising, reacting a hydrocarbyl vinylmercuric compound, with a palladium (II) dimerization promoting agent, said reaction being conducted in a polar organic solvent and in the presence of an additional source of halide ions.

2. The method of claim 1 wherein said palladium (II) dimerization promoting agent is a palladium (II) halide salt.

3. The method of claim 2 wherein said palladium (II) halide salt is palladium (II) chloride.

4. The method of claim 1 wherein said solvent is a phosphorus containing highly polar organic solvent.

5. The method of claim 4 wherein said solvent is hexamethylphosphoramide.

6. The method of claim 1 wherein said additional halide ions are chloride ions.

7. The method of claim 6 wherein the source of said chloride ions is an alkali metal chloride salt.

8. The method of claim 7 wherein the alkali method chloride salt is lithium chloride.

9. The method of claim 1 wherein said reaction is conducted at a temperature within the range of from about 0° C. to about 25° C.

10. The method of claim 9 wherein said reaction is conducted at about 0° C.

11. A method of preparing stereospecific, symmetrical conjugated hydrocarbyl 1,3 dienes, said method comprising reacting a vinylmercuric hydrocarbyl halide, with a palladium (II) halide salt, in a polar organic phosphorous containing solvent, and in the presence of a lithium halide salt, said 1,3 diene predominantly retaining the stereochemistry of said vinylmercuric halide.

12. The method of claim 11 wherein said solvent is hexamethylphosphoramide.

13. The method of claim 12 wherein said halide salts are chloride salts.

14. The method of claim 13 wherein said reaction is conducted at a temperature within the range of from about 0° C. to about 25° C.

* * * * *